United States Patent
Branham et al.

(10) Patent No.: US 8,331,620 B2
(45) Date of Patent: Dec. 11, 2012

(54) APPARATUS, SYSTEM, AND METHOD FOR AUTOMATIC AIRBORNE CONTAMINANT ANALYSIS

(75) Inventors: Robert Branham, Provo, UT (US); David Branham, Provo, UT (US)

(73) Assignee: Liberty Standard, LLC, Provo, UT (US)

( * ) Notice: Subject to any disclaimer, the term of this patent is extended or adjusted under 35 U.S.C. 154(b) by 605 days.

(21) Appl. No.: 12/616,693

(22) Filed: Nov. 11, 2009

(65) Prior Publication Data

US 2011/0110558 A1  May 12, 2011

(51) Int. Cl.
*G06K 9/00* (2006.01)

(52) U.S. Cl. ........................ 382/103; 356/436
(58) Field of Classification Search ........... None
See application file for complete search history.

(56) References Cited

U.S. PATENT DOCUMENTS

| | | | |
|---|---|---|---|
| 4,350,507 A | 9/1982 | Greenough et al. | |
| 4,475,379 A | 10/1984 | Jinotti | |
| 5,001,463 A | 3/1991 | Hamburger | |
| 5,646,597 A | 7/1997 | Hamburger et al. | |
| 6,288,646 B1 | 9/2001 | Skardon | |
| 6,594,001 B1 | 7/2003 | Yabusaki | |
| 2005/0251347 A1* | 11/2005 | Perona et al. | 702/19 |
| 2008/0304752 A1* | 12/2008 | Matteoni et al. | 382/209 |

FOREIGN PATENT DOCUMENTS

EP  1184659 A1  3/2009

OTHER PUBLICATIONS

Sander H. Landsmeer et al. "Detection of Pollen Grains in Multifocal Optical Microscopy Images of Air Samples" Microscopy Research and Technique Journal, Jan. 2, 2009.

* cited by examiner

*Primary Examiner* — Andrew W Johns
*Assistant Examiner* — Siamak Harandi
(74) *Attorney, Agent, or Firm* — Kunzler Law Group PC

(57) ABSTRACT

An apparatus, system, and method are disclosed for locating, classifying, and quantifying airborne contaminants. In one embodiment, the apparatus contains an air sampler, an imaging device, a processing module, and a user interface. The air sampler may contain at least one opening into which ambient air is flowable. The imaging device may produce images of the ambient air within an interior volume of the air sampler. The processing module may receive the images produced by the imaging device and may locate, classify, and quantify specific airborne contaminants, such as mold and pollen spores. Data concerning the airborne contaminants can be output to a user at a user interface.

20 Claims, 10 Drawing Sheets

APPARATUS, SYSTEM, AND METHOD FOR AUTOMATIC AIRBORNE CONTAMINANT ANALYSIS

FIELD

This invention relates to automatic analysis of airborne contaminants, and more particularly relates to detecting, locating, classifying, and quantifying airborne pollen and mold allergens.

BACKGROUND

Pollinosis, or hay fever, is caused by an allergic reaction by the body to pollen grains which are spread by insects, wind, and other means. When pollens, molds, and other allergens are taken into the body, the body fights to rid itself of the allergen. The immune system initiates a defense which may cause uncomfortable symptoms such as runny nose, watery eyes, congestion, itching, headache, joint pain, stomach pain or cramps, and sneezing. The severity of an allergic reaction can vary from mild discomfort to life threatening situations. In certain situations, an allergic reaction can cause choking of the voice or muscle spasm, which can lead to tightening of the throat and lungs, as occurs with asthma.

Approximately 15-20% of the population suffers from hay fever. Children also suffer from hay fever at an alarming rate. In 2007, 7.4 million children in the United States alone suffered from hay fever. Importantly, children with even minor allergies are at much greater risk of developing serious health problems when they reach adulthood. These serious problems include such life threatening health problems such as asthma, sinusitis, and ear infections. It is important that children are treated for allergies when they first show symptoms. Early treatment can lower the risk that the child will develop more serious health problems.

Pollen grains are not the only airborne contaminants which can cause serious health problems. Airborne mold, air pollution, smoke, dust mites, and other airborne contaminants also pose serious health problems to those who are exposed to them.

Due to the large number of people affected by airborne contaminants and the severe health effects caused by untreated exposure, agencies have begun to test air and publish test results. For example, institutions have begun to publish pollen and mold counts for specific areas. These numbers are used to indicate when an adult must be careful to avoid exposure to pollen and mold. Importantly, these numbers are also used by parents to help protect their children during times of high pollen levels.

Measurement of pollen and mold spores, which range from 3-250 microns in size, has been undertaken by some institutions with specialized equipment. Even the most advanced equipment and methods, however, require very expensive equipment and lab analysis by trained scientists. These institutions have made efforts to make pollen counts and other air quality measurements available to the public by means of, for example, publishing pollen counts for general areas, such as large metropolitan areas. These counts, however, are limited to the area directly surrounding the testing facility, are often not published promptly, and cover very small geographic regions of the world. Many people's homes and work environments fall outside of the reach of these pollen counts. As such, people outside the test areas and their children are left without accurate information and cannot adequately prepare to protect themselves through appropriate medication and other precautions.

SUMMARY

From the foregoing discussion, it should be apparent that a need exists for an apparatus, system, and method that automatically analyzes airborne contaminants, including pollen and mold, so that information that pertains to local air quality can be collected and used locally by a user. Beneficially, such an apparatus, system, and method would not require separate analysis and testing by scientists for each air test taken and could be used locally by a user.

The present invention has been developed in response to the present state of the art, and in particular, in response to the problems and needs in the art that have not yet been fully solved by currently available airborne contaminant testing technology. Accordingly, the present invention has been developed to provide an apparatus, system, and method to analyze airborne contaminants that overcome many or all of the above-discussed shortcomings in the art.

An apparatus for analyzing airborne contaminants is provided. The apparatus, in one embodiment, includes an air sampler, an imaging device, a processing module, and at least one user interface. In one embodiment, the air sampler defines a sample space through which ambient air is flowable. In one embodiment, the imaging device is coupled to the air sampler in image collecting communication with ambient air in the sample space of the air sampler. The imaging device captures at least one image of ambient air in the sample space.

In one embodiment, the processing module receives at least one image from the imaging device. The processing module determines the quantity of at least one type of airborne contaminant visible in the at least one image from the imaging device. In one embodiment, the at least one user interface receives information from the processing module concerning the quantity of at least one type of airborne contaminant in the at least one image. The information is accessible by a user of the user interface.

The apparatus is further configured, in one embodiment, such that the air sampler contains a housing. The housing contains a sample space and at least one opening through which ambient air is received by the sample space. The housing also contains non-adhesive surfaces.

In a further embodiment, the air sampler may be configured to contain a photographic background opposite the imaging device. In another embodiment, the imaging device captures at least one image of ambient air in the sample space while the ambient air is freely flowing within the sample space.

The apparatus is further configured, in one embodiment, such that the imaging device contains a digital microscope. In one embodiment, the digital microscope produces images with between one and five megapixels. In another embodiment, the imaging device contains a digital camera which is connected with a microscope lens.

In a further embodiment, the processing module may be configured to automatically locate, automatically classify, and automatically quantify airborne contaminants in the at least one image using an object recognition algorithm. The object recognition algorithm analyzes at least the size, shape, and color of the airborne contaminants in the images created by the imaging device.

The apparatus is further configured, in one embodiment, such that the user interface displays a separate count for each of several different types of pollen and mold, a total pollen count, and an indication of the pollen level. In another embodiment, the user interface contains an input mechanism which allows a user to initiate a test. In another embodiment, the processing module is a computer located remotely from the air sampler, imaging device, and user interface, wherein the processing module receives at least one image from the imaging device through an internet connection.

In one embodiment, the processing module is a computer program which is run on a user's computer. The processing module compares model data with the at least one image produced by the imaging device to locate, classify, and quantify airborne contaminants.

A system of the present invention is also presented for analyzing airborne contaminants. The system may be embodied to contain a collection apparatus, a detection apparatus, an analysis station, and at least one user interface. In particular, the system, in one embodiment, includes a collection apparatus which contains a structure through which ambient air is flowable. The collection apparatus may also contain at least one open end and an open volume into which ambient air is flowable.

The system may further include a detection apparatus which produces at least one microscopic image of the ambient air within the collection apparatus and the contents of the ambient air within the collection apparatus.

In one embodiment, the system also includes an analysis station which receives the at least one image from the detection apparatus. The analysis station, in one embodiment, also performs at least one of automatically locating, automatically identifying, and automatically quantifying at least one type of airborne contaminant in the at least one image received from the detection apparatus.

The system may further include at least one user interface which displays at least one of data and images received from at least one of the detection apparatus and the analysis station.

In particular, the collection apparatus, in one embodiment, produces at least one microscopic image of ambient air within the collection apparatus and the contents of the ambient air while the ambient air and contents of the ambient air are freely flowing within the open volume of the collection apparatus.

In a further embodiment, the analysis station contains a user's computer and a computer program. In another embodiment, the airborne contaminants include at least one of pollen and mold.

The system may further include a detection apparatus which produces at least one microscopic image of the ambient air within the collection apparatus and contents of the ambient air at a specified focal length from the detection apparatus. In one embodiment, the focal length of the microscopic image can be adjusted by a user.

A method of the present invention is also presented for analyzing airborne contaminants. The method in the disclosed embodiments substantially includes the steps necessary to carry out the functions presented above with respect to the operation of the described apparatus and system. In one embodiment, the method includes flowing ambient air into an air sampler. The method also may include producing a microscopic image of the ambient air and content of the ambient air within the air sampler. The method may also include automatically locating airborne allergens within the image and automatically identifying at least one type of airborne allergen within the image. The method, in one embodiment, may also include automatically determining a quantity of at least one type of airborne allergen based on the identification of the at least one type of airborne allergen and automatically outputting the quantity of at least one type of airborne allergen to a user interface.

In a further embodiment, the method includes producing a microscopic image of flowing ambient air while the flowing ambient air flows into, resides in, or flows out of the air sampler. The method may also include automatically identifying at least one type of airborne allergen within the image by comparing portions of the image to model data previously collected regarding airborne allergens using an object recognition algorithm.

The method may also include producing a plurality of microscopic images of the ambient air and contents of the ambient air within the sampler. Each image of the plurality of images may be produced at a different instance in time. The quantities of at least one type of airborne allergen from each of the plurality of images are compared to produce an average quantity of the at least one type of airborne allergen over a period of time during which the plurality of images were produced.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Figure 1:
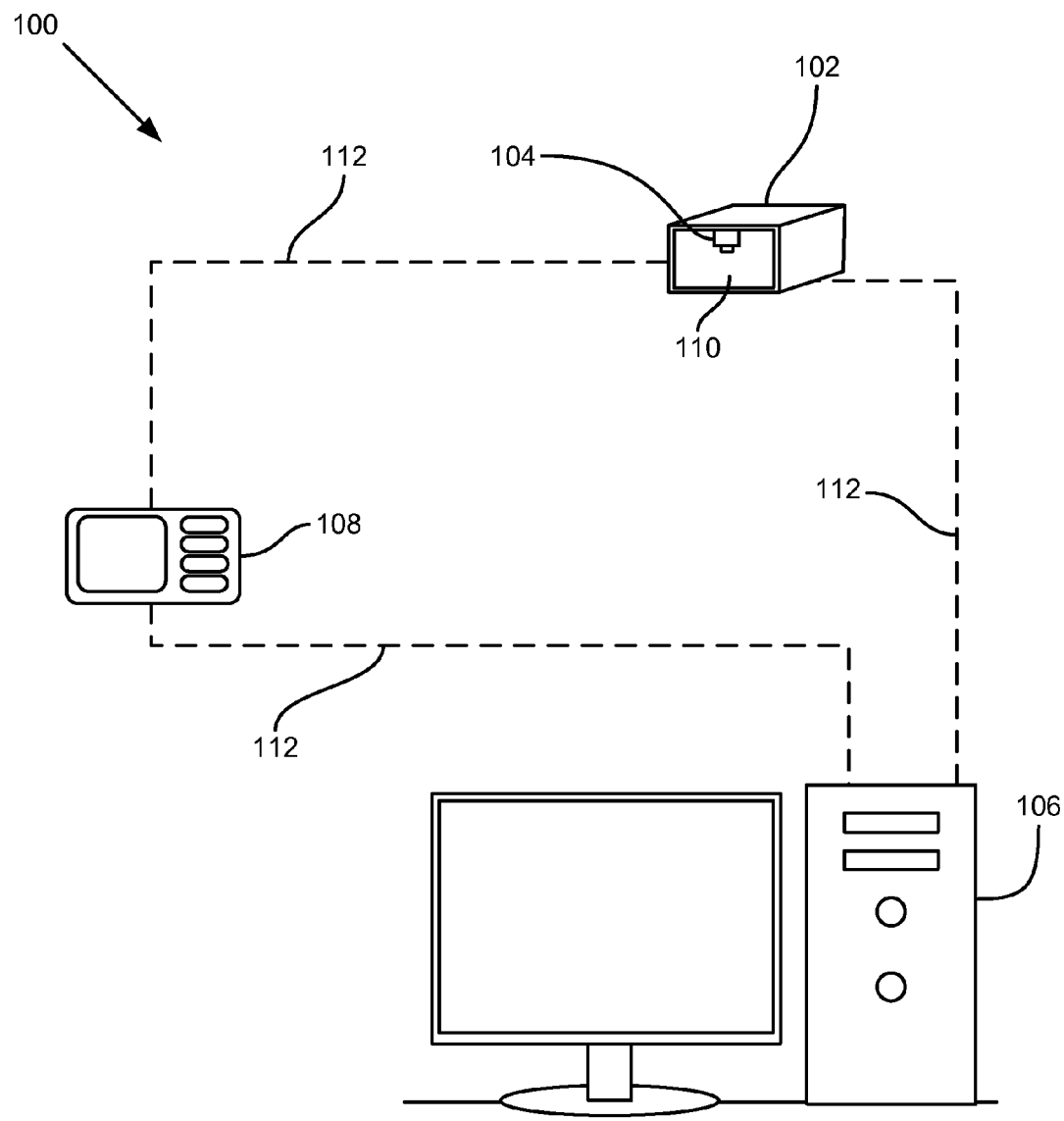
FIG. 1 is a schematic diagram of one embodiment of an apparatus for automatic airborne contaminant analysis.

FIG. 1 depicts one embodiment of an apparatus 100. The apparatus 100 contains an air sampler 102, an imaging device 104, a processing module 106, and a user interface 108. In one embodiment, the air sampler 102 contains at least one opening 110 so that air surrounding the apparatus 100 can enter the opening 110 within the air sampler 102. In other embodiments, the air sampler 102 is shaped differently, as will be shown is subsequent figures.

The imaging device 104 creates images of the air within the air sampler 102. Those images are sent, along with any additional imaging device data that has been collected by the imaging device 104, to the processing module 106. Data and images can be sent through any type of data transmission apparatus 112, including but not limited to a hardwire connection, blue tooth connection, internet connection, and wireless connection. As defined herein, imaging device data is data produced by the imaging device 104 and processing module data is data produced by the processing module 106. In certain embodiments, imaging device data is processed by the processing module 106 to produce processing module data. In certain embodiments, portions of processing module data are the same as portions of imaging device data. In certain embodiments, processing module data is the same as imaging device data. In certain embodiments, processing module data is different than imaging device data.

In one embodiment, the processing module 106 processes the images and imaging device data received from the imaging device 104. The processing module 106 produces processing module data by quantifying specific airborne contaminants within the images and imaging device data. The processing module data is output to at least the user interface 108 and may also be output to the imaging device 104, a user's computer, the air sampler 102, or other storage device. The user interface 108 displays at least one of imaging device data, processing module data, and images. The user interface 108 may also receive input from a user.

In one embodiment, the user interface 108 may be physically separate from a user's computer or may form part of the user's computer. One example of a separate user interface is a wall-mounted key pad. One example of a user interface on a user's computer is a computer program. The user can selectively operate the user interface 108 to request a test by the apparatus 100.

In certain embodiments, the apparatus 100 can be programmed by the user to automatically run multiple tests at intervals throughout the day. A test is a cycle of analyzing, such as locating, classifying, and quantifying, airborne contaminants. In other embodiments, the apparatus 100 is programmable to run tests at specific times set by the user. For example, a user may program the apparatus 100 to run several tests each morning and send an average of the processing module data to the user interface 108. When a test is completed, at least some portion of processing module data collected during the test is available to the user on a user interface 108. Processing module data and imaging device data that is output to a user through a user interface may be changed in form or content so that it is understandable and convenient to use by the user.

As defined herein, airborne contaminants may include pollen spores, mold spores, pollution, dust, small particulate insulation contaminants such as fiberglass and asbestos, dust mites, aerosol material, household cleaning product residue, smoke, or any other material which is not air that is found in air. Depending on the magnification used by the imaging device 104, different airborne contaminants may appear in the images produced by the imaging device 104. Depending on the embodiment, the apparatus 100 may search for, classify, and quantify different types of airborne contaminants, including, but not limited to, those listed above.

The apparatus 100 can be used to analyze different types of airborne allergens. In one embodiment, for example, the apparatus 100 is programmed to analyze pollen spores in ambient air. In another embodiment, for example, the apparatus 100 analyzes mold spores in ambient air. In one embodiment, the apparatus 100 can be programmed to locate specific types of airborne contaminants. In one embodiment, the apparatus 100 analyzes several different types of airborne contaminants. In one embodiment, for example, the apparatus 100 analyzes grass pollen, blue weed pollen, tree pollen, smoke, automobile pollution, dandelion pollen, and mold spores.

According to one embodiment, in operation, the air sampler 102 receives an inflow of ambient air. The imaging device 104 produces at least one image of the ambient air within the air sampler 102. The at least one image is sent to the processing module 106. The processing module 106 runs a computer program on the user's computer. The computer program scans the images to locate pollen and mold spores. Pollen and mold spores are differentiated from other airborne contaminants by their size, shape and color. The computer program may also differentiate between different types of pollen and different types of mold by analyzing the color, shape and size of the spores.

The processing module 106 then outputs processing module data concerning the number of each type of pollen and mold to the user interface 108. A user can view the user interface 108 and see the amount of each type of pollen and mold in the sampled air. A user with allergies to certain types of airborne allergens can then make informed decisions for the day by using the processing module data displayed on the user interface. The collected information is specific to the ambient air that was sampled. Depending on the location of the apparatus 100, such as a work office, a home, a child's bedroom, a classroom, or other area, a user can receive a pollen count, mold count, and count of any other airborne contaminant for which the processing module is programmed to search, that is specific to that area.

In one embodiment, the air sampler 102, imaging device 104, processing module 106 and user interface 108 can all be located in a user's home. In one embodiment, the air sampler 102, imaging device 104, processing module 106, and user interface 108 can also perform their functions without sending each image to a scientist, lab technician, or other trained person for data analysis. In one embodiment, the data processing of the processing module 106 is performed automatically on a user's home computer. In certain embodiments, this may allow for completely automatic, rapid testing, and analysis.

Figure 2:
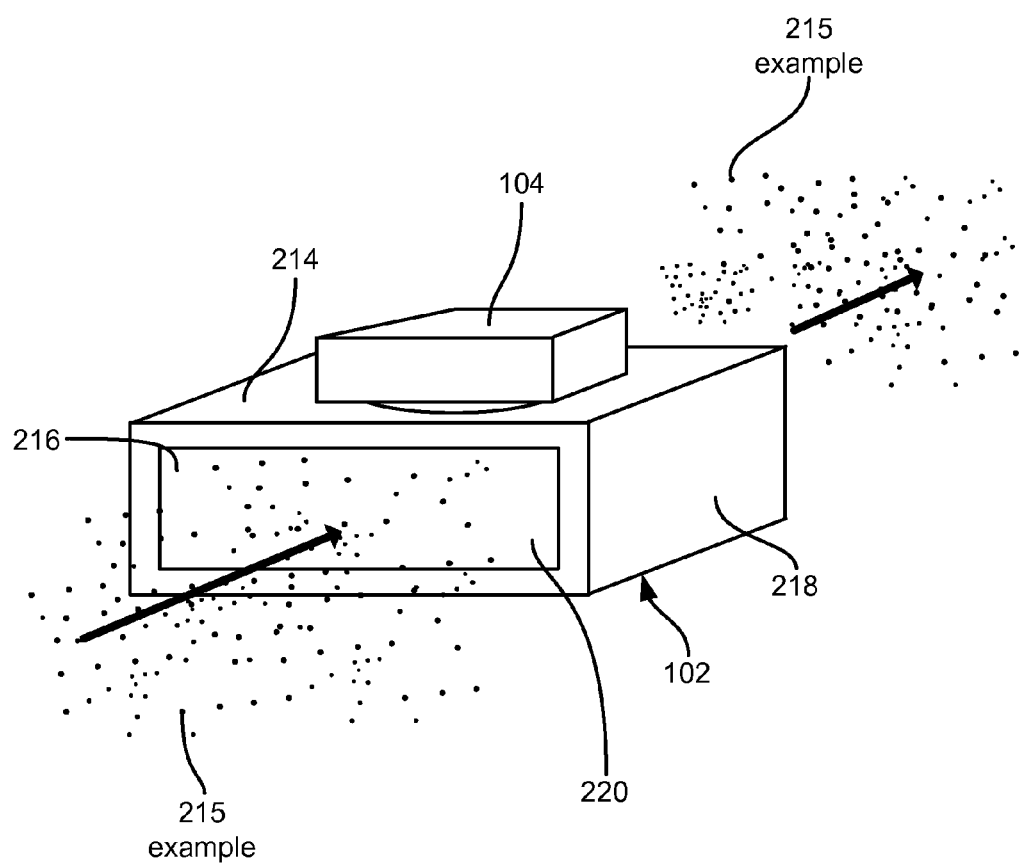
FIG. 2 is a perspective view of one embodiment of an air sampler and an imaging device in accordance with the present invention.

FIG. 2 shows a close up view of one embodiment of an air sampler 102 and attached imaging device 104. Particles 215 represent airborne contaminants contained in ambient air. As can be seen, ambient air is flowable into the air sampler 102. The air sampler 102 contains a housing 214 which, in the embodiment of FIG. 2, is rectangular in shape. The housing 214 has an inner surface 216 and an outer surface 218. In the embodiment of FIG. 2, the imaging device 104 is attached to a portion of the outer surface 218 of the air sampler 102.

In the embodiment of FIG. 2, ambient air is flowable through the housing 214. The housing 214 contains two openings, a first opening 220 and a second opening (not shown). Ambient air is flowable through the first opening 220, through a rectangular internal volume of the air sampler 102, and out the second opening. In this manner ambient air can flow through the apparatus 100 according to the natural airflow of the area in which the apparatus 100 is located. Because the ambient air is flowable through the air sampler 102, images taken by the imaging device 104 at different times in the day may contain different airborne contaminants.

In one embodiment, the housing 214 contains non-adhesive surfaces. In this manner, airborne contaminants do not adhere to the surfaces of the housing 214 in order for the imaging device 104 to produce an image of the airborne contaminants. Rather, the ambient air within the housing and the airborne contaminants within the ambient air are free flowing when photographed by the imaging device 102. As defined herein, free flowing can indicate normal, unadjusted airflow, as well as any type of forced air flow. Free flowing indicates that airborne contaminants within ambient air are not adhered to a surface in order for an image to be produced by the imaging device 104.

Figure 2A:
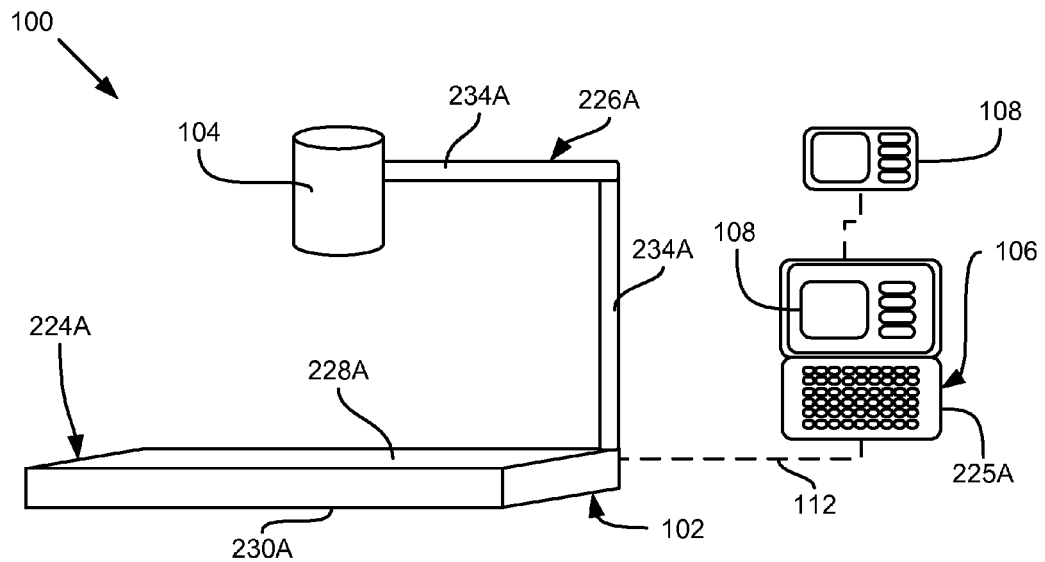
FIG. 2A is a front view of one embodiment of an air sampler connected to a processing module and a user interface in accordance with the present invention.
Figure 2B:
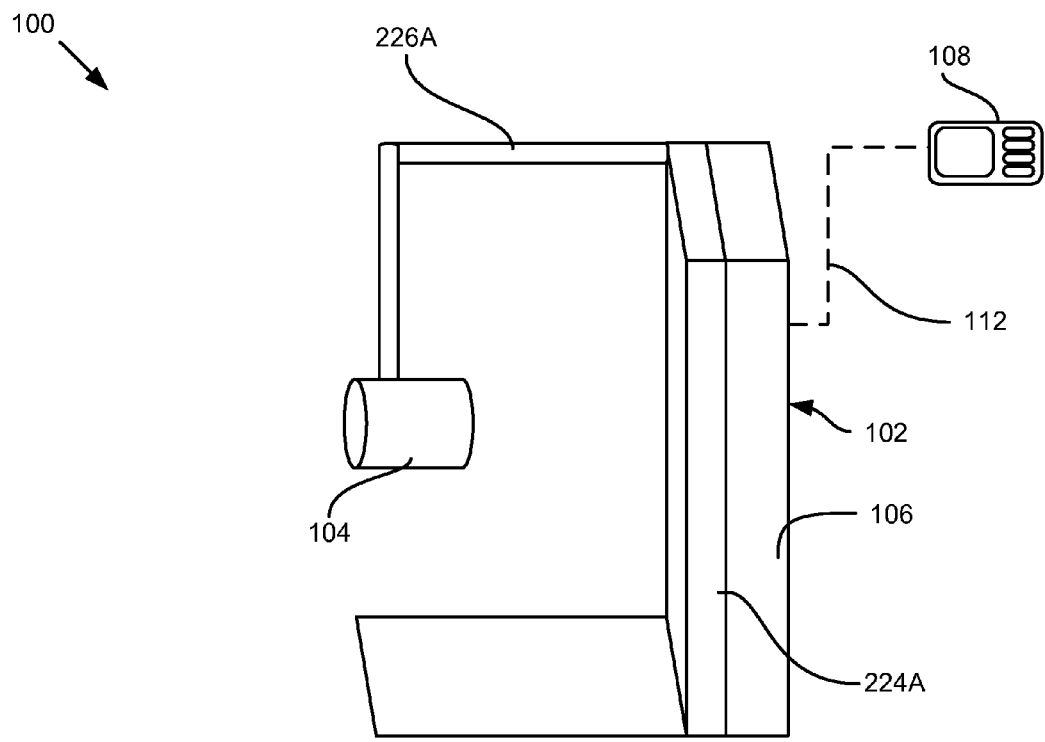
FIG. 2B is a front view of another embodiment of an air sampler connected to a user interface in accordance with the present invention.
Figure 2C:
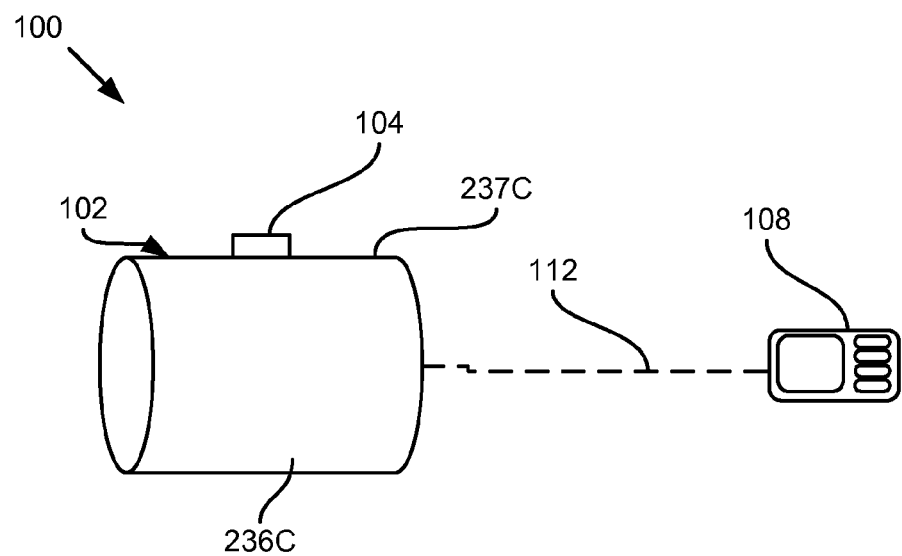
FIG. 2C is a side view of another embodiment of an air sampler connected to a user interface in accordance with the present invention.
Figure 2D:
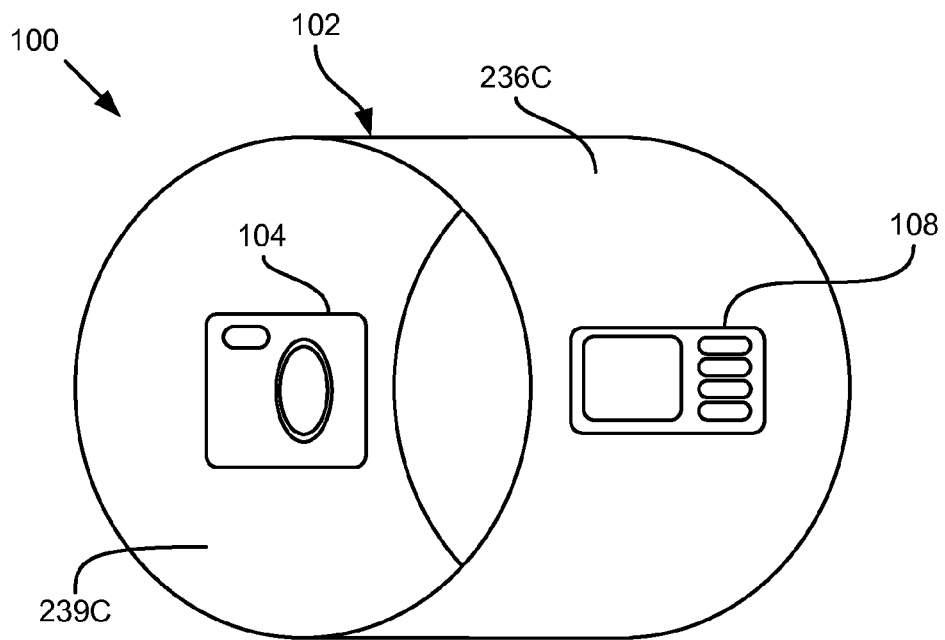
FIG. 2D is a perspective view of another embodiment of an air sampler which contains an imaging device and a user interface in accordance with the present invention.
Figure 2E:
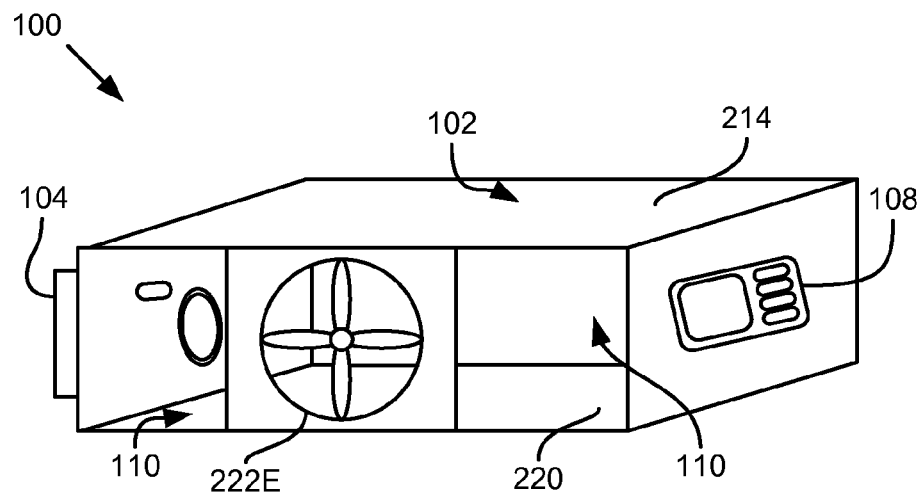
FIG. 2E is a perspective view of another embodiment of an air sampler which contains an imaging device and a user interface in accordance with the present invention.

In one embodiment, the air sampler 102 contains an air flow mechanism 222e such as a fan, as shown in FIG. 2E. The air flow mechanism 222E induces air flow into, out of, or through the air sampler 102. An airflow mechanism 222E may be necessary in areas of lower air flow. In other embodiments, an air flow mechanism 222e is not necessary.

In one embodiment, the air sampler 102 contains a photographic background within the housing 214. The photographic background is located on an inner surface 216 of the housing 214 opposite the imaging device 104 and, in one embodiment, is constructed of a material that reduces glare. In another embodiment, the photographic background is constructed of a white matte material. In another embodiment, the photographic background is constructed of a colored material. In another embodiment, the photographic background contains a light source.

In one embodiment, the air sampler 102 does not contain adhesive material used to capture airborne contaminants. Ambient air is flowable into the air sampler 102 and need not be adhered to a surface in order for the imaging device 104 to create an image of the contents of the ambient air. In one embodiment, the apparatus 100 automatically creates an image of the ambient air within the air sampler 102 as the ambient air is flowing through the air sampler 102, automatically analyzes that image in the processing module 106, and then automatically outputs at least one of imaging device data, processing module data, and images to the user interface 108. Because the apparatus 100 is automatic, it does not require removal of an adhesive surface or petri dish by the user to be sent to a lab for analysis. In one embodiment, because the airborne contaminants are not fixed to an adhesive surface, a dye is not applied to the contaminants to make them more easily identified.

In one embodiment, the air sampler 102 contains a light source. In one embodiment, the light source is used to increase contrast between the airborne contaminants and the photographic background. In one embodiment, the light source is a florescent light source which causes the airborne contaminants to fluoresce. In one embodiment, the light source is a colored light source. In one embodiment, the light source is located opposite from the imaging device 104. In another embodiment, the light source is located on a same side of the air sampler 102 as the imaging device 104. In one embodiment, the light source is a strobe light. In this embodiment, image exposure is controlled by the speed of the light source in conjunction with the shutter speed of the imaging device 104.

In one embodiment, the air sampler 102 and the imaging device 104 are sufficiently small in size to be placed indoors. In one embodiment, the air sampler 102 is one foot by six inches by six inches. In another embodiment, the air sampler 102 is six inches by five inches by five inches. The apparatus 100 can be used in household indoor environments, in commercial department store environments, in educational facilities, in libraries, or any other indoor facility. In other embodiments, the apparatus 100 can be used in any outdoor application. In one embodiment, the air sampler 102 contains a waterproof and weather proof housing 214.

The embodiments of FIGS. 2A through 2F show different embodiments of the air sampler 102 and imaging device 104. In the embodiment of FIG. 2A, the air sampler 102 contains a base 224A and an arm 226A. The base 224A is a rectangular sheet which contains an upper surface 228A and a lower surface 230A. In certain embodiments, the upper surface 228A acts as a background for images produced by the imaging device 104.

The arm 226A extends upward from a corner of the base 224A to support the imaging device 104. The arm 226A may have a plurality of sections 234A or a single section 234A, depending on the embodiment. In the embodiment of FIG. 2a, the arm 226a has two sections 234A which are oriented at an angle to each other. In certain embodiments, the arm 226A is adjustable so that the user and manufacturer can orient the imaging device 104. The imaging device 104 is attached to the arm 226A and faces the base 224A such that the imaging device 104 can produce images of the ambient air between itself and the base 224A.

In the embodiment of FIG. 2A, images and imaging device data produced by the imaging device 104 can be sent wirelessly, through the internet, through hardwired data transmission, or any other type of data transmission, to a processing module 106 contained on a personal computer 225A. At least one of imaging device data, processing module data, and images can be viewed on a user interface 108 on the user's computer or on a separate user interface 108.

In the embodiment of FIG. 2B, the air sampler 102 again contains a base 224A and an arm 226A. In contrast to the embodiment of FIG. 2A, the base 224A in the embodiment of FIG. 2B contains the processing module 106 and thus does not require a connection with an external computer or other external processing module 106. The processing module 106 is attached to the base 224A of the air sampler 102. In another embodiment, the processing module 106 is part of the base 224A. The processing module data is output to a separate user interface 108. In another embodiment, the air sampler 102 may also contain a user interface 108 (not shown) integrated into the base 224A.

Also in contrast to the embodiment of FIG. 2A, the embodiment of FIG. 2B shows the imaging device 104 in a lateral position as opposed to a vertical position, as shown in FIG. 2A. The base 224A and the processing module 106 are oriented in a vertical orientation.

In the embodiment of FIG. 2C, the air sampler 102 contains a cylindrical housing 236C. The imaging device 104 is attached to an outer surface 237C of the cylindrical housing 236C and produces images of ambient air within an interior volume of the air sampler housing 236C. The processing module 106 (not shown) is contained within the air sampler housing 236C. The processing module 106 (not shown) outputs at least one of processing module data and images to the separate user interface 108.

In the embodiment of FIG. 2D, the air sampler 102 again contains a cylindrical housing 236C. The imaging device 104 is attached to an interior surface 239C of the cylindrical housing 236C and produces images of ambient air within an interior volume of the air sampler 102. The imaging device 104 is attached to a lateral portion of the housing 236C. The user interface 108 is contained within an outer surface of the cylindrical housing 236C. In one embodiment, the processing module 106 (not shown) is also contained within the cylindrical housing 236C of the air sampler 102. In another embodiment, the processing module 106 (not shown) is contained within a personal computer of the user.

In the embodiment of FIG. 2E, the air sampler 102 contains a housing 214 in the shape of a rectangular box. The housing 214 contains one opening 220, a user interface 108, and an attached imaging device 104. The housing 214 also contains an airflow mechanism 222E used to induce air flow into the air sampler 102. The imaging device 104 is attached to a lateral side of the housing 214. The airflow mechanism 222E can induce airflow into or out of the housing 214. A user interface 108 is contained on an outer surface of a lateral side of the housing 214.

Figure 2F:
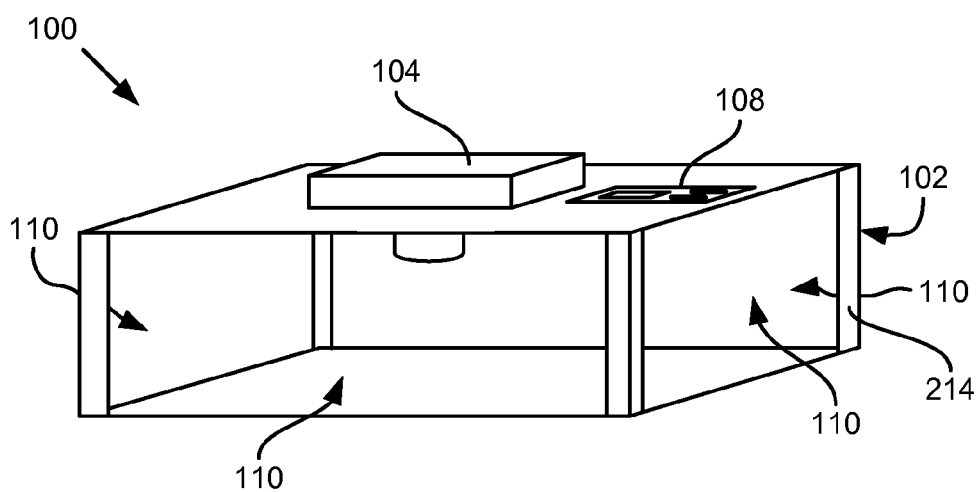
FIG. 2F is a perspective view of another embodiment of an air sampler which contains an imaging device and a user interface in accordance with the present invention.

As mentioned above, the air sampler 102 contains at least one opening 110 into which ambient air is flowable. In the embodiment of FIG. 2F, the air sampler 102 contains a housing 214 with four large openings 110. In other embodiments, the air sampler 102 may contain more openings 110 or may be completely open, as shown in FIGS. 2A and 2B.

Returning to FIG. 2, the image device 104 is shown attached to the air sampler 102. In one embodiment, the imaging device 104 can create at least one of images and imaging device data concerning the ambient air in the air sampler 102. In one embodiment, the imaging device 104 produces microscopic images of flowing ambient air while the flowing ambient air flows into or out of the air sampler 102. In this embodiment, the ambient air and its contents are not adhered to a surface in order for an image to be produced, but rather the image is produces at a certain focal length while the air is flowing. Airborne contaminants within the flowing air are not adhered to an adhesive surface and may be stationary or moving within the ambient air.

In one embodiment, the imaging device 104 is oriented such that it creates images of the ambient air in the air sampler 102. The imaging device 104 can be located on any portion of the air sampler 102. In the embodiment of FIG. 2, the imaging device 104 is located on a top portion of the air sampler 102. In the embodiments of FIGS. 2D and 2E, the imaging device 104 is located on a lateral side of the air sampler 102. In another embodiment, the imaging device 104 is located on a bottom portion of the air sampler 102. In the embodiments of FIGS. 2A and 2B, the imaging device 104 is held over the base 224A of the air sampler 102 by an arm 226A.

Figure 3:
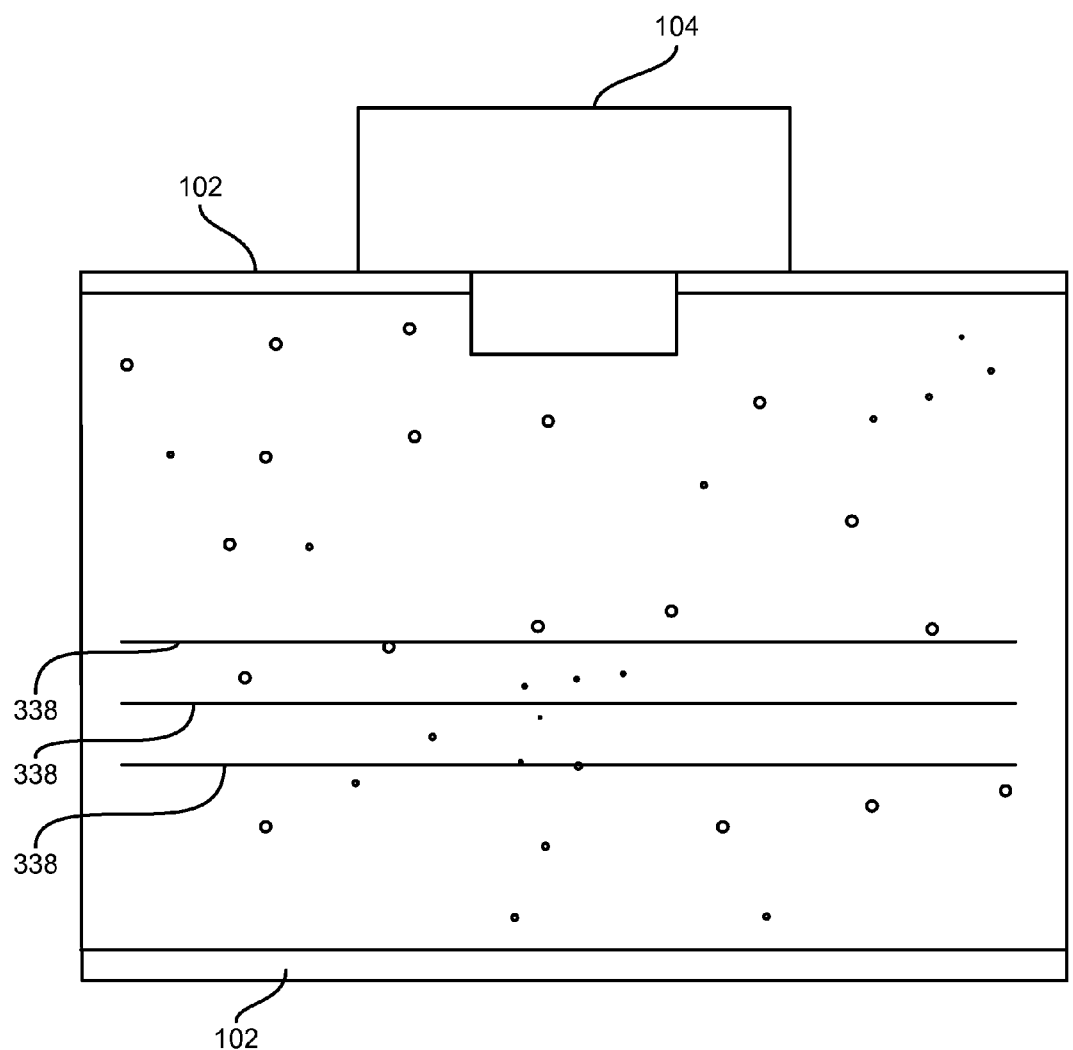
FIG. 3 is a cutaway side view of one embodiment of an air sampler and imaging device in accordance with the present invention.

In the embodiments of FIGS. 2 and 3, the imaging device 104 is attached to an exterior surface of the air sampler 102. In one embodiment, an opening in the air sampler 102 allows the imaging device 104 to create images of the ambient air in the air sampler 102. In other embodiments, including the embodiment of FIG. 1, the imaging device 104 is contained within the air sampler 102 and is attached to an internal surface of the air sampler 102. In yet another embodiment, the imaging device 104 is integrated into the air sampler 102 such that the imaging device 104 does not attach to either the inside surface or outside surface of the air sampler 102, but is integrated into a surface of the air sampler 102.

The imaging device 104 may be battery powered or may be hardwired to a typical power outlet. In one embodiment, the imaging device 104 can be programmed to create images using different image capturing modes to highlight different features of the airborne contaminants. In different embodiments, for example, images can be created in a light mode, an scanning electron microscope (SEM) mode, a transmission electron microscope (TEM) mode, or an edge detect mode. In one embodiment, the imaging device 104 can create imaged in more than one capturing mode. One of skill in the art will recognize other modes which can be used to highlight different features of the airborne contaminants in accordance with the present invention.

In one embodiment, the imaging device 104 is a camera. In another embodiment, the imaging device 104 is a microscope camera. In one embodiment, the imaging device 104 is a digital microscope camera. In one embodiment, the imaging device 104 is not microscope camera but is a personal use camera with a microscope attachment used to allow the camera to produce magnified images. This embodiment may be used to lower the cost of the imaging device 104. In another embodiment, the imaging device 104 is a digital microscope. In one embodiment, the digital microscope contains one or more eye pieces for viewing by a user. In another embodiment, the digital microscope does not contain an eye piece but simply outputs an image to the processing module 106.

In certain embodiments, the imaging device 104 contains a dedicated camera. A dedicated camera is a camera which is connected with a computing device, either through a hardwired connection or a wireless connection, and which stores images produced by the camera directly onto the computing device rather than storing the images onto storage within the camera. In other embodiments, the imaging device 104 contains a digital camera which stores images onto data storage within the digital camera. In these embodiments, the digital camera may be connected to a computing device by the user or by the manufacturer, through either a hardwired or wireless connection, to transfer images from the camera storage to the computer device. In another embodiment, the imaging device 104 stores images on a removable data storage device which can be transferred to another location, such as a secure digital card (SD card). In any of these embodiments, a computing device to which images are saved or transferred may be the processing module 106. In one embodiment, the computer to which stored images are transferred is not the processing module 106. In this embodiment, the computer to which stored images are transferred sends the images to the processing module 106.

In one embodiment, the imaging device 104 contains a microscope capable of up to 400× magnification. In another embodiment, the imaging device 104 contains a microscope capable of up to 1000× magnification. In one embodiment, the magnification of the imaging device 104 can be adjusted according to the size of airborne contaminants to be analyzed.

In one embodiment, the imaging device 104 is a Celestron LCD Digital Microscope, Item #44340, which is manufactured by Celestron®. In another embodiment, the imaging device 104 is a Veho VMS-004 Discovery Series 400× USB microscope which is manufactured by Veho. One of skill in the art will recognize other devices that can be used as the imaging device 104.

In one embodiment, the imaging device 104 produces images with between one and five megapixels. In one embodiment, the imaging device 104 produces images with more than five megapixels. In one embodiment, the imaging device 104 can be programmed to produces images with fewer megapixels in order to decrease processing time. In one embodiment, the imaging device 104 produces images with approximately three megapixels.

FIG. 3 shows a cutaway view of one embodiment of an air sampler 102 and an imaging device 104. In one embodiment, the imaging device 104 can produce multiple images at different focal lengths (represented by lines 338), as shown in FIG. 3. In one embodiment, the imaging device 104 can be programmed to make images of the air within the air sampler 102 at different focal lengths from the imaging device 104. The lines 338 represent different focal lengths at which images may be produced. In certain embodiments, images are produces at focal lengths that differ by only about four micrometers so that the adjacent images can be compared by the processing module 106. In another embodiment, the imaging device 104 can produce multiple images at different focal lengths in a short period of time. These images can be compared in the processing module 106. In one embodiment, the imaging device 104 can produce multiple images at the same focal length. In one embodiment, the images are produced with a step size of about four micrometers.

In one embodiment, the imaging device 104 is capable of sequential shooting to allow for several images to be produced in a short period of time. In one embodiment, the shutter speed of the imaging device 104 is approximately 2 frames per second. In one embodiment, the shutter speed of the imaging device 104 is adjustable. In another embodiment, only single images are produced by the imaging device 104.

Figure 4:
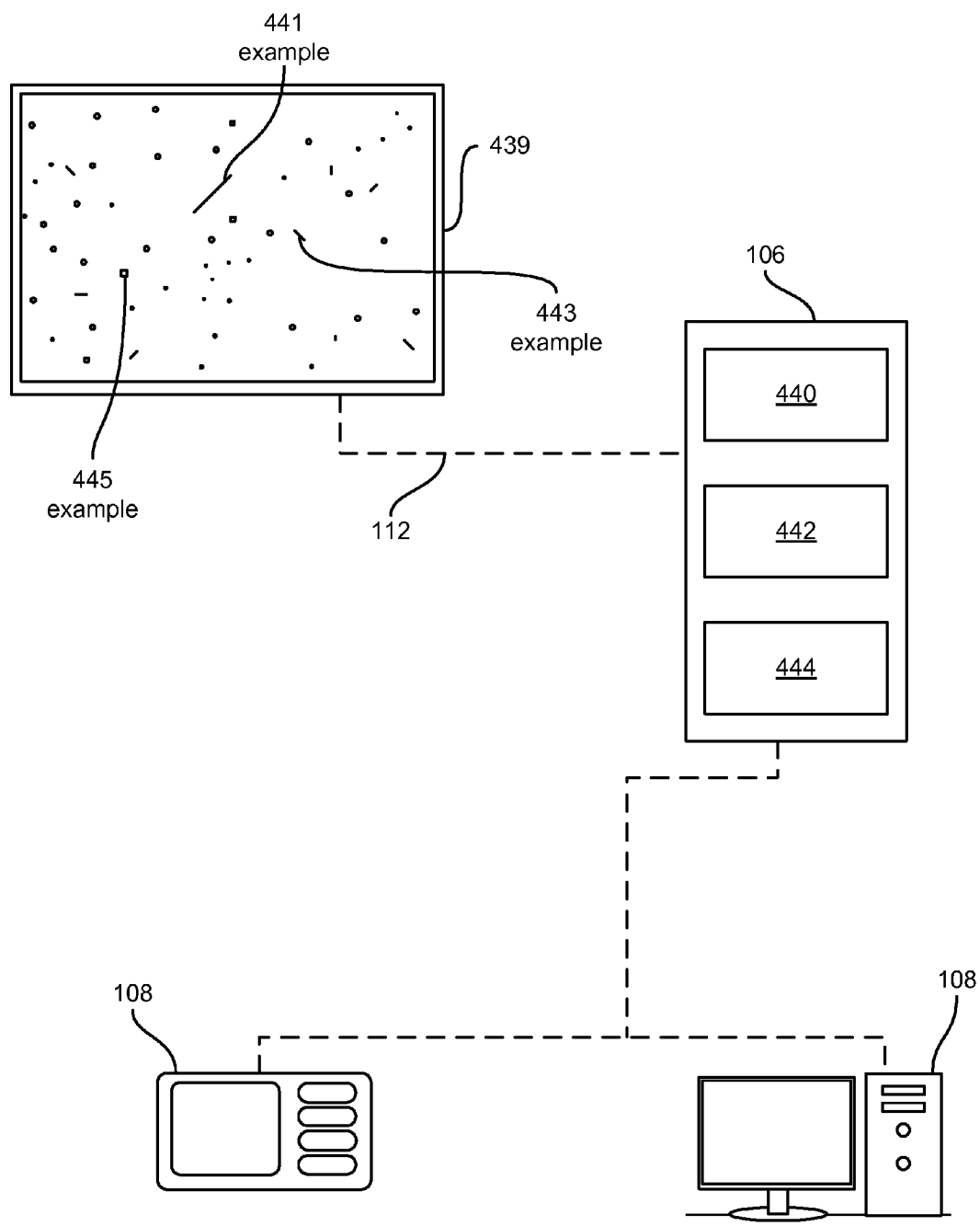
FIG. 4 is a schematic diagram of one embodiment of the processing module connected to an image and two user interfaces in accordance with the present invention.

FIG. 4 shows one embodiment of the processing module 106 in connection with a user interface 108 and an image 439. The processing module 106 receives at least one of imaging device data and images 439 from the imaging device 104 (not shown). In one embodiment, the processing module 106 contains at least one of a locating module 440, a classifying module 442, and quantifying module 444 used to locate, classify, and quantify, respectively, airborne contaminants in at least one of the images and imaging device data created by the imaging device 104. In one embodiment the processing module 106 processes the images and imaging device data from the imaging device 104 automatically.

In one embodiment, the processing module 106 scans the image to locate objects of a certain size, shape and color. In one embodiment, predetermined size, shape, and color model data is compared to imaging device data and images from the imaging device, in order to determine the type and amount of airborne contaminants in the image. As defined herein, model data is data that has been collected from another source. In one embodiment, the model data is collected in order to be compared with images and imaging device data produced by the imaging device 104. Model data may come from photographs of airborne contaminants, from laboratory tests performed on airborne contaminants, or from other sources of information regarding airborne contaminants. In one embodiment, model data is collected from external sources and programmed into the processing module to be automatically compared with imaging device data and images collected by the imaging device. As defined herein, model images are images that have been collected from another source.

In one embodiment, the processing module 106 compares airborne contaminants from the images produced by the imaging device 104 with model data and model images to determine if airborne contaminants in the images produced by the imaging device 104 match airborne contaminants from model images and model data. In one embodiment, for example, model data and model images concerning size, shape, and color of grass pollen is collected from an external source. The model data and model images are made available to the processing module 106. When the processing module 106 scans images from the imaging device 104, the processing module 106 compares airborne contaminants from the model images and model data with the imaging device data and images. If a specific feature in the imaging device data and images closely matches grass pollen data from the model data, the processing module 106 flags that feature as grass pollen. A similar approach can be taken with all different types of airborne contaminants.

In many instances, the ambient air sampled by the air sampler 102 will contain dirt, pollution, and other non-pollen particles, as represented by particles 441, 443, and 445. In this case, the processing module 106 identifies, as accurately as possible, the sought after airborne contaminants from among all the airborne contaminants.

In one embodiment, the processing module 106 performs an object recognition algorithm. In one embodiment, the processing module 106 first scans the image for a particular shape of airborne contaminant. When an airborne contaminant is found that fits the shape description, at least one verification step is performed by the processing module 106. Verification steps can include analyzing color, surface smoothness, size, color consistency, transparency, surface ornamentation, aperture type, aperture number, number of walls, and thickness of walls. If the airborne contaminant is verified as the sought after airborne contaminant, the processing module adds to the number of that airborne contaminant.

In another embodiment, the processing module 106 performs a different object recognition algorithm. The processing module 106 scans the image for a plurality of shapes. When an airborne contaminant is found that fits one of the plurality of shapes, at least one verification step is performed to classify the airborne contaminant. Once the airborne contaminant is classified, the quantity of that airborne contaminant is increased to reflect the newly classified airborne contaminant. The processing module 106 then continues to scan the image for other airborne contaminants.

In one embodiment, the processing module 106 uses object recognition software to analyze imaging device data and images. In one embodiment, the processing module 106 utilizes Speeded Up Robust Features (SURF) object recognition software. In another embodiment, the processing module 106 utilizes Scale-invariant Feature Transform (SIFT) object recognition software. One of skill in the art will recognize other object recognition software that can be used by the processing module 106 to analyze different types of airborne contaminants within imaging device data and images.

The proceeding algorithms and processes performed by the processing module 106 represent only some of the possible embodiments used to analyze airborne contaminants by the processing module 106. Different object recognition algorithms and methods can be used by the processing module 106 to analyze airborne contaminants in the images produced by the imaging device.

In one embodiment, the processing module 106 is part of the air sampler 102. In another embodiment, the processing module 106 is separate from the air sampler 102. In yet another embodiment, the processing module 106 is a computer program that is run on a computer. In another embodiment, the processing module 106 is an internet site. In another embodiment, the processing module 106 is a server.

Figure 5:
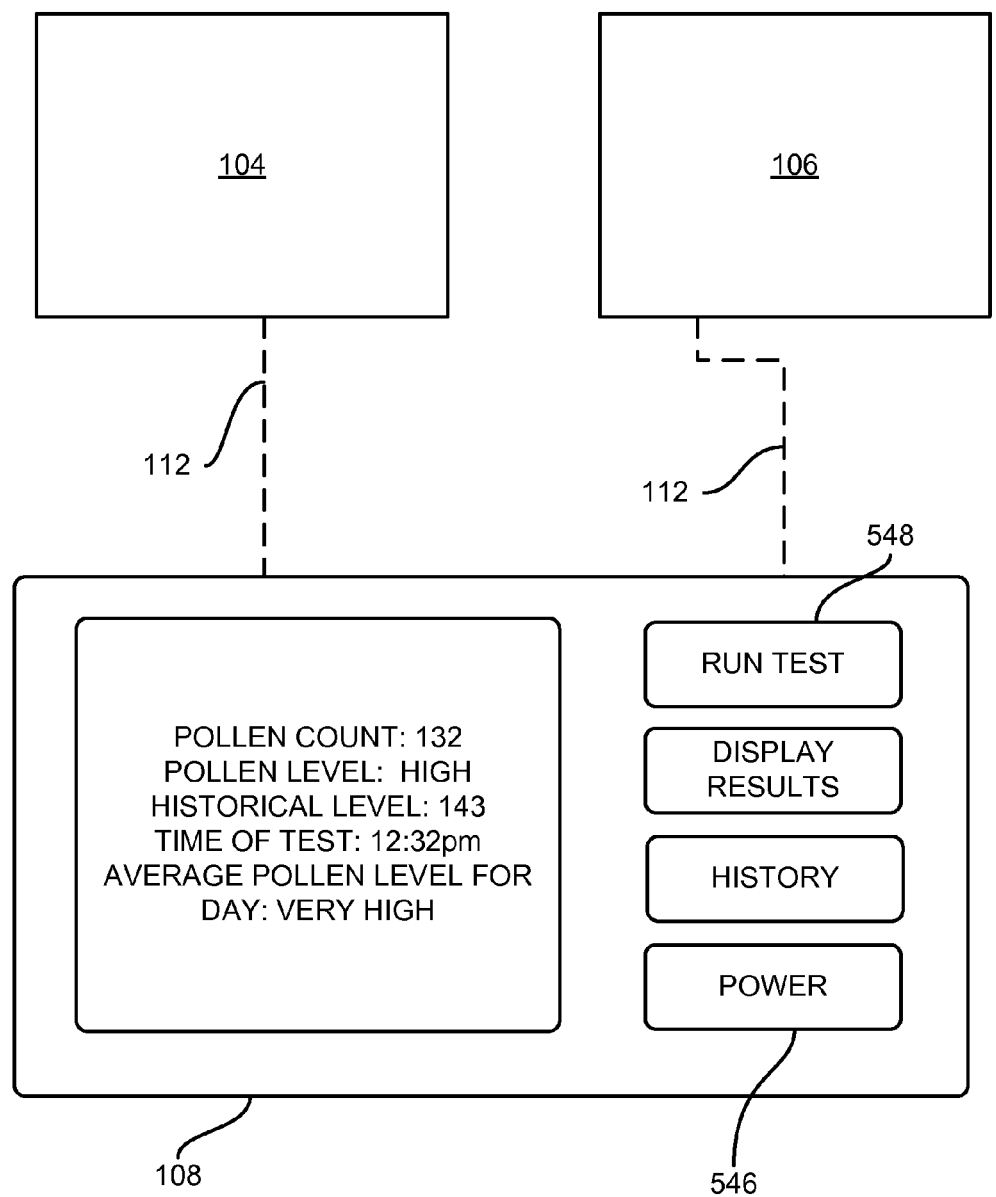
FIG. 5 is a front view of one embodiment of a user interface connected to an imaging device and a processing module in accordance with the present invention.

FIG. 5 shows one embodiment of a user interface 108 connected with the processing module 106 and the imaging device 104. The user interface 108 receives at least one of imaging device data, images, and processing module data from at least one of the imaging device 104 and the processing module 106. In one embodiment, the user interface 108 receives images from the imaging device 104 which are then displayed to the user on the user interface 108. In another embodiment, the user interface 108 receives processing module data from the processing module 106 which is the displayed to the user. In one embodiment, the user interface 108 receives images, imaging device data, and processing module data, which are displayed to the user.

In one embodiment, the user interface 108 receives user input in addition to displaying data and images. The user interface 108, for example, may contain a power button 546 which allows the user to turn the imaging device 104 on and off. The user interface 108 may contain a run button 548 which allows a user to indicate that the imaging device 104 should produce images and processing device data and process the images and data in the processing module 106.

In one embodiment, the user interface 108 may display a total pollen count, an indication of the pollen level, the historical pollen level for the day, the time of the last pollen test, and the average pollen level for the day. In another embodiment, the user interface 108 may display a separate count for each of several different types of pollen, mold, and other airborne contaminants. In one embodiment, the user interface 108 contains a light that indicates high levels of pollen.

In one embodiment, there are several user interfaces which receive at least one of imaging device data, processing module data, and images from at least one of the imaging device and the processing module. In one embodiment, for example, a cell phone, an email address, a portable computer, a television, and a wall-mounted input device all act as user interfaces which display at least one of data and images and receive user input. In other embodiments, other objects which allow a user to view information can act as a user interface.

Figure 6:
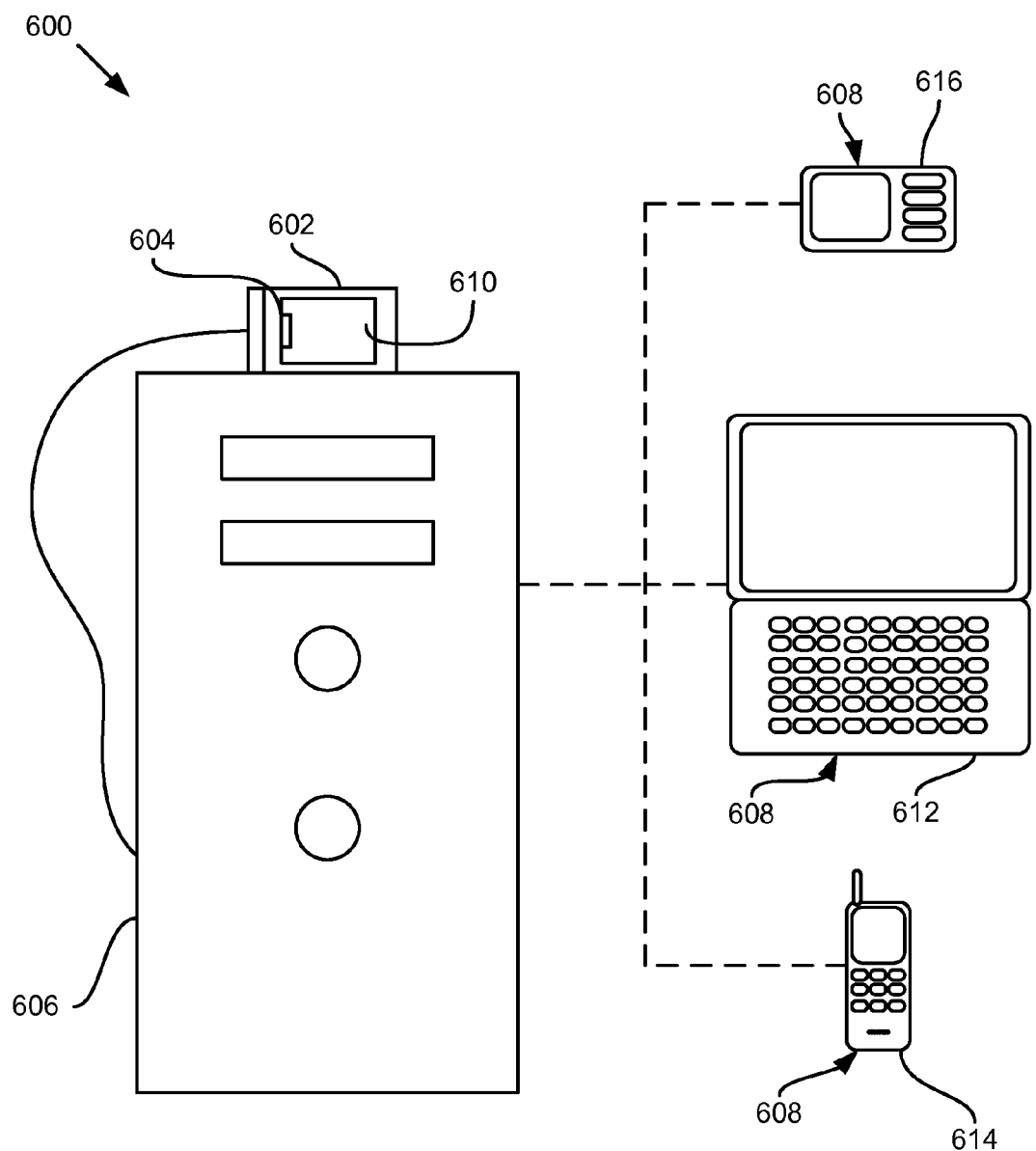
FIG. 6 shows one embodiment of a system for automatic analysis of airborne contaminants in accordance with the present invention.

FIG. 6 shows one embodiment of a system 600 to analyze airborne contaminants in accordance with the present invention. In one embodiment, the system 600 contains a collection apparatus 602, a detection apparatus 604, an analysis station 606, and several user interfaces 608.

The collection apparatus 602 contains a structure through which ambient air is flowable. In one embodiment, the collection apparatus 602 contains at least one opening 610 into which ambient air is flowable. In the embodiment of FIG. 6, the collection apparatus 602 contains two openings 610 such that air is flowable in and out of the openings and into and out of an internal volume. The collection apparatus 602 does not contain an adhesive material used to collect airborne contaminants. An adhesive may, however, be used in the construction of the collection apparatus 602.

The system 600 also contains a detection apparatus 604 which produces images of the ambient air within the collection apparatus 602. In one embodiment, the detection apparatus 604 is a digital camera that is contained within a lateral wall of the collection apparatus 602. The detection apparatus 604 may be any mechanism capable of producing magnified images of the ambient air and airborne contaminants in the ambient air.

The system 600 also contains an analysis station 606 which receives at least one of data and images from the detection apparatus 602. In the embodiment of FIG. 6, the analysis station 606 is a computer program that is run on the personal computer. The analysis station 606 performs at least one of locating, identifying and quantifying airborne contaminants in at least one of the data and images received from the detection apparatus 602.

The data collected by the analysis station 606 is output to a user interface 608. The data output by the analysis station 606 may include several types of information, including but not limited to, images, processed information, and operational instructions. The user interfaces 608 displays at least one of data and images received from either the detection apparatus 604 or the analysis station 606.

The embodiment of FIG. 6 shows several different types of user interfaces 608. In one embodiment, a personal computer 612 may be the user interface 608. In another embodiment, the analysis station 606 may wirelessly transmit information to a user's portable phone 614. In another embodiment, the analysis station 606 transmits information to a user's portable computer 612. In another embodiment, the analysis station 606 emails information to a user's email address. In another embodiment, the analysis station 606 transmits information to several different types of user interfaces 608. In one embodiment, the analysis station 606 transmits information to several wall-mounted keypads 616 within a user's home or business. In one embodiment, the analysis station 606 transmits information to a security system which is installed in a user's home and contains wall-mounted keypads. In another embodiment, the analysis station 606 transmits information to a user's television. One of skill in the art will recognize other user interface 608 options which can receive data from the detection apparatus 604 or the analysis station 606. In one embodiment, the analysis station 606 is programmable to send information to the user interface 608 periodically throughout a day.

Figure 7:
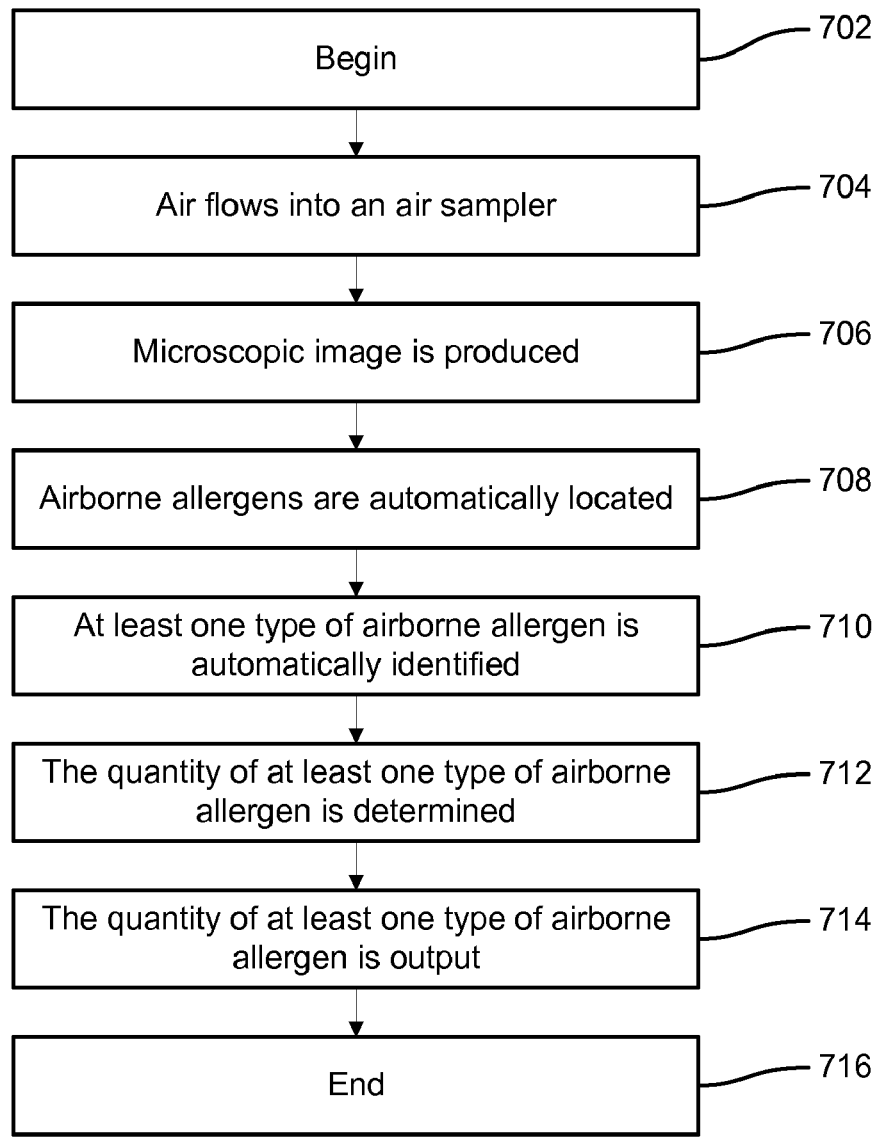
FIG. 7 is a schematic block diagram illustrating one embodiment of a method for automatic analysis of airborne contaminants in accordance with the present invention.

FIG. 7 shows one embodiment of a method 700 in accordance with the present invention. The method 700 begins 702 and air flows 704 into an air sampler 102. A microscopic image of the air is produced 706. In one embodiment, the microscopic image is an image that has been magnified. In one embodiment, the image contains an image of the air and any airborne contaminants contained within the air. Airborne allergens are automatically locating 708 within the image. At least one type of airborne allergen is automatically identified 710 within the image. The quantity of at the least one type of airborne allergen is determined 712 based on the identification of the at least one type of airborne allergen. The quantity of at least one type of airborne allergen is output 714 to a user interface and the method 700 ends 716.

In one embodiment, the method 700 also includes producing a microscopic image of flowing ambient air while the flowing ambient air flows into or out of the air sampler. In this embodiment, the ambient air and its contents are not adhered to a surface in order for an image to be produced but rather the image is produces at a certain focal length while the air is flowing.

In another embodiment, the method includes automatically identifying the type of certain airborne allergens within the image by comparing portions of the image to test data previously collected regarding certain airborne allergens. In one embodiment, for example, the size, shape, and color of a mustard pollen spore are collected from test data. That test data is automatically compared to portions of the microscopic image to determine if any of the airborne contaminants within the image are mustard pollen. If a certain number of mustard pollen spores are located, that number is output to a user interface.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the above description, numerous specific details are provided, such as examples of programming, physical structure, connections between components, user selections, data transmission mechanisms, hardware modules, etc., to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus for analyzing airborne contaminants, the apparatus comprising:

an air sampler defining a sample space through which ambient air is flowable;

an imaging device coupled to the air sampler in image collecting communication with ambient air in the sample space, wherein the imaging device captures at least one image of ambient air in the sample space;

a processing module receiving at least one image from the imaging device, wherein the processing module determines the quantity of at least one type of airborne contaminant visible in the at least one image; and at least one user interface receiving information from the processing module concerning the quantity of at least one type of airborne contaminant in the at least one image, the information being accessible by a user of the at least one user interface.

2. The apparatus of claim 1, wherein the air sampler comprises a housing containing the sample space, the housing comprising at least one opening through which ambient air is received by the sample space, wherein the housing contains non-adhesive surfaces.

3. The apparatus of claim 1, wherein the air sampler comprises a photographic background opposite the imaging device and a light source.

4. The apparatus of claim 1, wherein the imaging device captures at least one image of ambient air in the sample space while the ambient air is freely flowing within the sample space.

5. The apparatus of claim 1, wherein the imaging device further comprises a digital microscope.

6. The apparatus of claim 5, wherein the digital microscope produces images with between one and five megapixels.

7. The apparatus of claim 1, wherein the imaging device further comprises a digital camera connected with a microscope lens.

8. The apparatus of claim 1, wherein the processing module automatically locates, automatically classifies, and automatically quantifies airborne contaminants in the at least one image using an object recognition algorithm that analyzes at least the size, shape, and color of the airborne contaminates in the images created by the imaging device.

9. The apparatus of claim 1, wherein the at least one user interface displays a separate count for each of several different types of pollen and mold, a total pollen count, and an indication of the pollen level.

10. The apparatus of claim 1, wherein the processing module is a computer located remotely from the air sampler, imaging device, and user interface, wherein the processing module receives at least one image from the imaging device through an internet connection.

11. The apparatus of claim 1, wherein the processing module is a computer program run on a user's computer, wherein the processing module compares model data with the at least one image produced by the imaging device to locate, classify, and quantify airborne contaminants.

12. A system for analyzing airborne contaminants, the system comprising:

a collection apparatus which comprises a structure through which ambient air is flowable, the collection apparatus comprising at least one open end and an open volume into which ambient air is flowable;

a detection apparatus which produces at least one microscopic image of the ambient air within the collection apparatus and contents of the ambient air within the collection apparatus;

an analysis station receiving the at least one image from the detection apparatus, wherein the analysis station performs at least one of automatically locating, automatically identifying, and automatically quantifying at least one type of airborne contaminant in the at least one image received from the detection apparatus; and at least one user interface displaying at least one of data and images received from at least one of the detection apparatus and the analysis station.

13. The system of claim 12, wherein the collection apparatus produces the at least one microscopic image of ambient air within the collection apparatus and contents of the ambient air while the ambient air and contents of the ambient air are freely flowing within the open volume of the collection apparatus.

14. The system of claim 12, wherein the analysis station further comprises a user's computer and a computer program.

15. The system of claim 12, wherein airborne contaminants includes at least one of pollen and mold.

16. The system of claim 12, wherein the detection apparatus produces at least one microscopic image of the ambient air within the collection apparatus and contents of the ambient air at a specified focal length from the detection apparatus, wherein the focal length of the microscopic image can be adjusted by a user.

17. A method for analyzing airborne contaminants, the method comprising:
flowing ambient air into an air sampler;
producing a microscopic image of the ambient air and contents of the ambient air within the air sampler;
automatically locating airborne allergens within the image;
automatically identifying at least one type of airborne allergen within the image;
automatically determining a quantity of at least one type of airborne allergen based on the identification of the at least one type of airborne allergen; and
automatically outputting the quantity of at least one type of airborne allergen to a user interface.

18. The method of claim 17, wherein the method comprises producing a microscopic image of flowing ambient air while the flowing ambient air flows into, resides in, or flows out of the air sampler.

19. The method of claim 17, wherein the method comprises automatically identifying at least one type of airborne allergen within the image by comparing portions of the image to model data previously collected regarding airborne allergens using an object recognition algorithm.

20. The method of claim 17, wherein the method comprises producing a plurality of microscopic images of the ambient air and contents of the ambient air within the sampler, wherein each image of the plurality of images is produced at a different instance in time, wherein quantities of at least one type of airborne allergen from each of the plurality of images are compared to produce an average quantity of the at least one type of airborne allergen over a period of time during which the plurality of images were produced.

* * * * *